Figure 1:
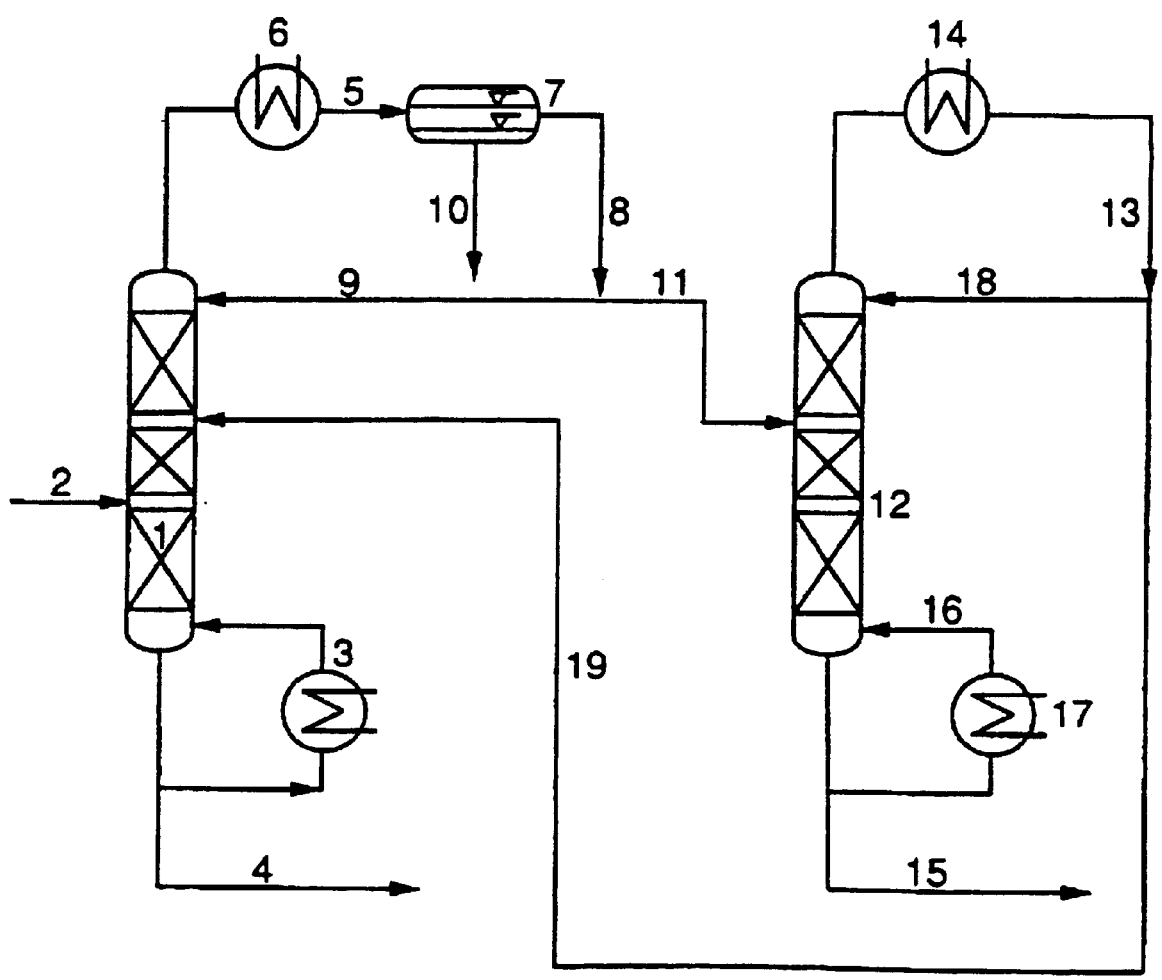

United States Patent
Aron et al.

[11] Patent Number: 5,985,100
[45] Date of Patent: Nov. 16, 1999

[54] PROCESS FOR SEPARATING BUTANOL AND DIBUTYL ETHER BY MEANS OF DUAL-PRESSURE DISTILLATION

[75] Inventors: Maik Aron, Freinsheim; Harald Rust, Neustadt, both of Germany

[73] Assignee: BASF Aktiengesellschaft, Ludwigshafen, Germany

[21] Appl. No.: 09/011,700

[22] PCT Filed: Aug. 26, 1995

[86] PCT No.: PCT/EP96/03762

§ 371 Date: Feb. 17, 1998

§ 102(e) Date: Feb. 17, 1998

[87] PCT Pub. No.: WO97/08120

PCT Pub. Date: Mar. 6, 1997

[30] Foreign Application Priority Data

Aug. 30, 1995 [DE] Germany ............... 195 31 787

[51] Int. Cl.$^6$ ............... B01D 3/00; C07C 29/80; C07C 41/42
[52] U.S. Cl. ............... 203/74; 203/75; 203/77; 203/78; 203/80; 203/99; 203/DIG. 19; 203/14; 568/698; 568/699; 568/916; 568/918
[58] Field of Search ............... 203/14, 18, 73, 203/78, 80, 77, 99, 75, DIG. 19, 42, 74; 568/913, 698, 699, 916; 56/918

[56] References Cited

U.S. PATENT DOCUMENTS

| | | |
|---|---|---|
| 2,356,348 | 8/1944 | Patterson . |
| 2,552,412 | 5/1951 | Drout . |
| 2,610,141 | 9/1952 | Drout, Jr. . |
| 2,875,138 | 2/1959 | Altreuter . |
| 4,282,389 | 8/1981 | Droste et al. ............... 568/697 |
| 4,308,109 | 12/1981 | Griffiths et al. ............... 203/78 |
| 4,448,644 | 5/1984 | Foster et al. ............... 203/DIG. 19 |

FOREIGN PATENT DOCUMENTS 974 477  7/1949  Germany .

OTHER PUBLICATIONS

Derwent Abs.AN 70–24101R.

Primary Examiner—Virginia Manoharan
Attorney, Agent, or Firm—Keil & Weinkauf

[57] ABSTRACT

Butanol and dibutyl ether are separated from a mixture containing water, dibutyl ether and n-butanol, 2-butanol and/or isobutanol by a process in which
a) the mixture is introduced into a first distillation column, essentially butanol is separated off at the bottom of this distillation column and the mixture taken off at the top of the distillation column
b) is introduced into a second distillation column and essentially dibutyl ether is separated off at the bottom of this second distillation column and the mixture formed at the top of the second distillation column is removed,
c) the second distillation column being operated at a higher pressure than the first distillation column and at least one of the two mixtures taken off via the top of the distillation columns being subjected to phase separation, only the organic phase separated off being fed to the second distillation column in the case of phase separation downstream of the first distillation column, and separation into an aqueous and an organic phase also being effected in the case of phase separation downstream of the second distillation column, a part stream being recycled from the top or rectification section of the second distillation column to the first distillation column.

14 Claims, 4 Drawing Sheets

PROCESS FOR SEPARATING BUTANOL AND DIBUTYL ETHER BY MEANS OF DUAL-PRESSURE DISTILLATION

The present invention relates to an improved process for separating butanol and dibutyl ether from a mixture containing water, dibutyl ether and n-butanol, 2-butanol and/or isobutanol.

Butanols are widely used in the chemical industry, and the use as solvents in coatings and as starting material for the synthesis of plasticizers are typical examples.

The large scale industrial production of butanol is carried out predominantly by hydroformylation of propene and subsequent hydrogenation to butanol, and is described, for example, in D1 (Chem. Ing. Techn., 41st year, 1969, pages 974–980, Dr. Dümbgen, Dr. Neubauer, GroBtechnische Herstellung von Oxo-Alkoholen aus Propylen in der BASF). In the process described here, it is proposed to separate butanol from mixtures which contain dibutyl ether and water by extraction with water and then to separate butanol and water by distillation (page 978, second section). However, this separation process proves to be relatively expensive where large amounts have to be separated off, since the extraction requires large amounts of water as an extracting agent, which have to be subsequently separated off again by distillation.

In the non prior published German patent application D2 (O.Z. 0050/44548, file reference P 4400837.6), a process for the preparation of n-butyraldehyde and/or n-butanol starting from 1,3-butadiene is described. There, the butanol preparation is carried out finally in stage d) of the process, an enol ether being converted in the presence of water and hydrogen (page 24, lines 8 to 34). The resulting mixture also contains dibutyl ether and water in addition to butanol and must be separated before further processing.

It is an object of the present invention to provide an improved process which permits the separation of butanol and dibutyl ether from mixtures containing butanol, dibutyl ether and water by a procedure which is simple and economical in terms of process engineering. It is a further object of the present invention to enable butanol or dibutyl ether to be isolated in high purity, the introduction of additional water being avoided.

We have found that these objects are achieved by a process for separating butanol and dibutyl ether from a mixture containing water, dibutyl ether and n-butanol, 2-butanol and/or isobutanol, wherein
a) the mixture is introduced into a first distillation column, essentially butanol is separated off at the bottom of this distillation column and the mixture taken off at the top of the distillation column
b) is introduced into a second distillation column and essentially dibutyl ether is separated off at the bottom of this second distillation column and the mixture formed at the top of the second distillation column is removed,
c) the second distillation column being operated at a higher pressure than the first distillation column and at least one of the two mixtures taken off via the top of the distillation columns being subjected to phase separation, only the organic phase separated off being fed to the second distillation column in the case of phase separation downstream of the first distillation column, and separation into an aqueous and an organic phase also being effected in the case of phase separation downstream of the second distillation column, a part stream being recycled from the top or rectification section of the second distillation column to the first distillation column.

Figure 2:
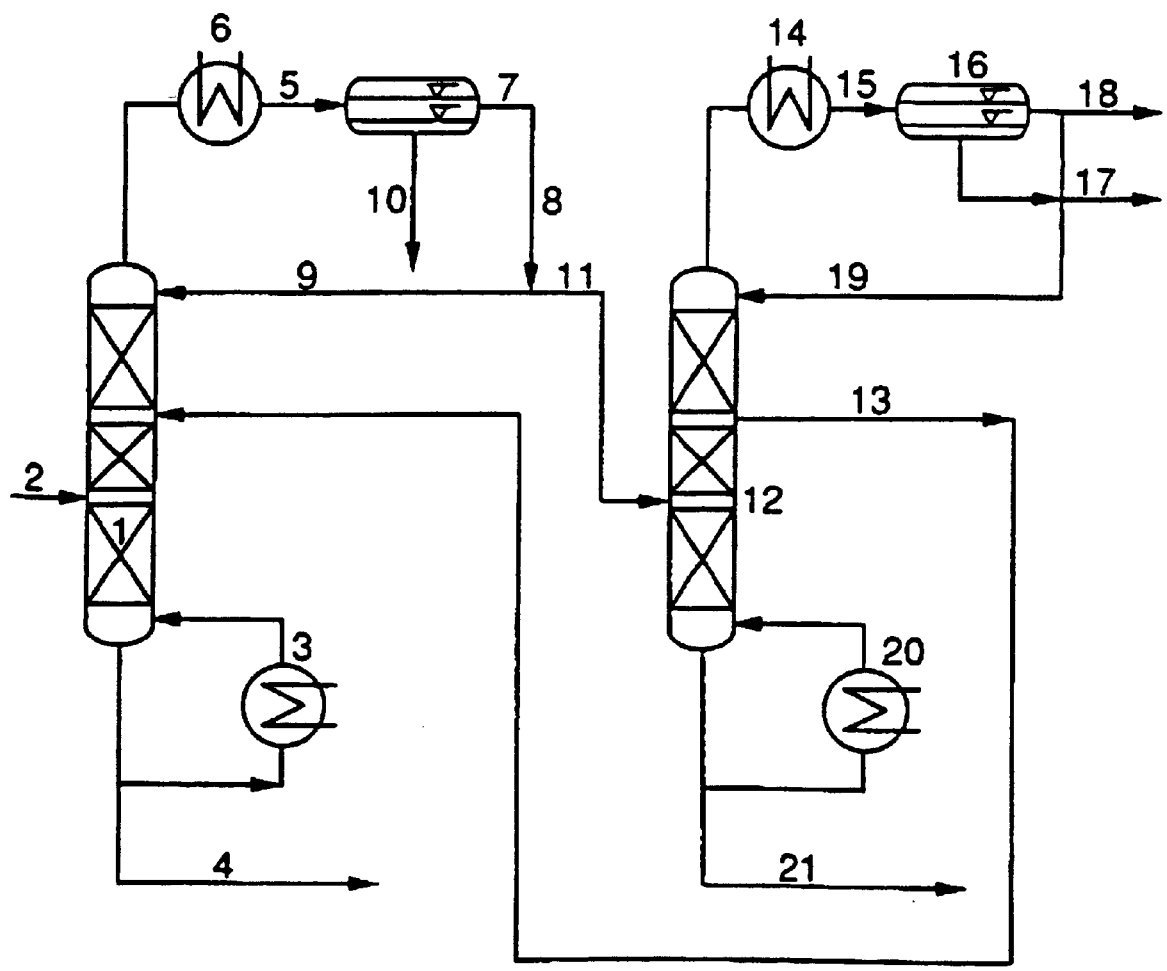

FIGS. 1 and 2 show arrangements for distillation columns suitable for carrying out the present process.

Figure 3:
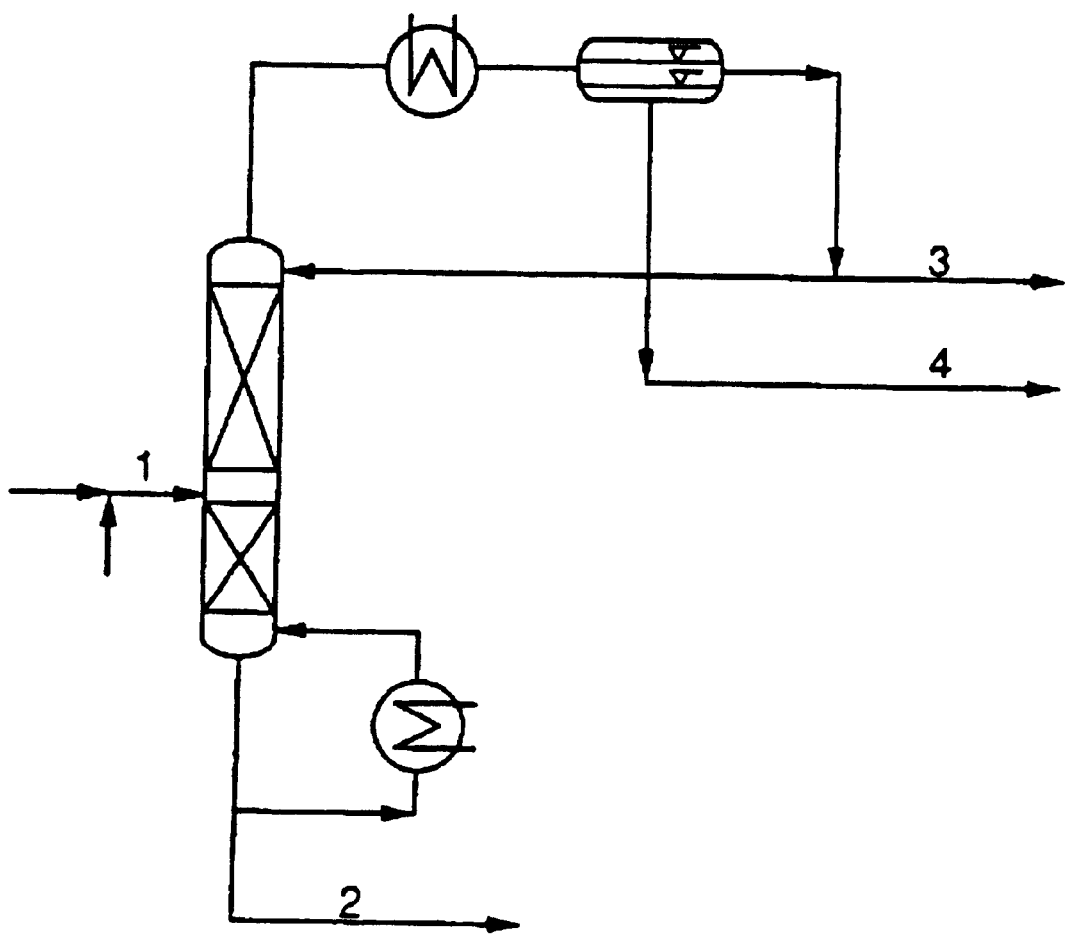
Figure 4:
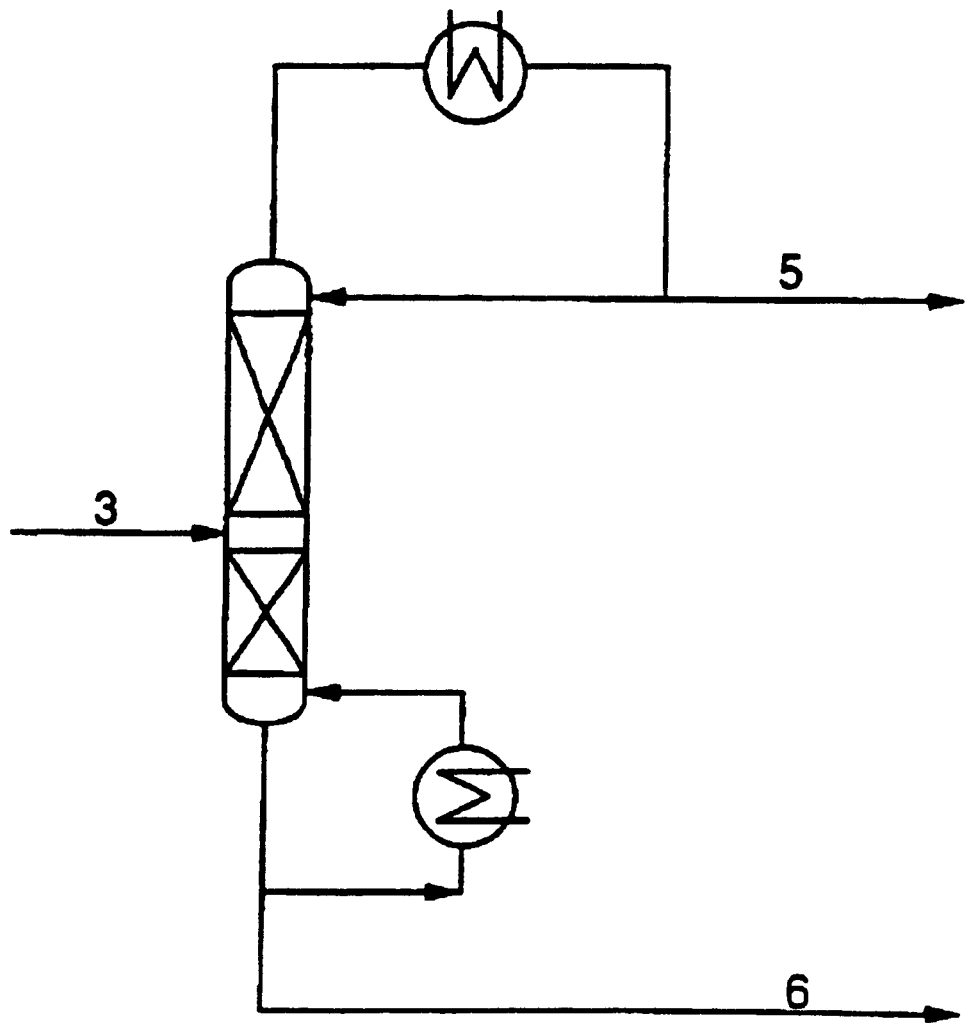

FIGS. 3 and 4 schematically set out the arrangement for the distillation in laboratory scales. FIG. 3 particularly sets forth the arrangement of the first distillation column and FIG. 4 represents an arrangement for the second distillation column.

The novel process is described in detail by way of example below with reference to FIG. 1.

A mixture which contains essentially butanol, dibutyl ether and water is fed to a distillation column (1) by means of pipe (2). Mixtures which contain from about 20 to 99, preferably from 70 to 95%, by weight of butanol, from 0.05 to 50, preferably from 0.5 to 10%, by weight of dibutyl ether and from 0.05 to 50, preferably from 1 to 20%, by weight of water are particularly suitable for the novel process. Virtually pure butanol is taken off, by means of pipe (4), at the bottom of the column (1), which is connected in a conventional manner to an evaporator (3). Usually, the concentrations of butanol are from about 80 to 100, preferably from 95 to 99.99%, by weight. The remaining components are composed essentially of traces of dibutyl ether and residues of water.

The first distillation column is usually operated at a pressure of from about 0.02 to 2, preferably from 0.1 to 0.7, bar at the top of the column. The temperatures in the column are from about to 100° C. at the top of the column and from about 65 to 110° C. at the bottom of the column. In general, conventional columns are suitable for the separation. Conventional baffles, such as commercial packings or trays, may be used.

The size of the column depends on the respective throughputs. The number of theoretical plates in the column is from about 10 to 70, preferably from 15 to 50, particularly preferably from 25 to 40.

A product stream which, depending on the mode of operation of the column, advantageously has virtually the azeotropic concentration is taken off at the top of the column via pipe (5) and condenser (6).

The literature discloses that mixtures of butanol, water and dibutyl ether form ternary azeotropes. For example D3 (Advances in Chemistry Series No. 116, Azeotropic Data III, 1973, pages 468 to 473, ISBN 8412-0166-8) provides more exact data in this context. The Table below shows the azeotropic concentrations of some mixtures of substances at a given pressure and temperature.

| Water (% by wt.) | Di-n-butyl ether (% by wt.) | n-Butanol (% by wt.) | 2-Butanol (% by wt.) | Temperature (° C.) | Pressure (mbar) |
| --- | --- | --- | --- | --- | --- |
| 29.9 | 35.5 | 34.6 | | 90.6 | 1000 |
| 31.2 | 44.2 | 24.6 | | 45 | 130 |
| 24.7 | 19.2 | | 56.1 | 86.6 | 1000 |

The composition of the product stream taken off by the top is thus continuously influenced by the prevailing temperatures and pressures and by the type of components present, for example it is important whether n-butanol or 2-butanol is present. Furthermore, the mode of operation of the column, for example the energy supply, influences the composition. The composition, which has virtually the azeotropic concentration, therefore cannot in general be exactly quantified.

The product stream taken off at the top of the column is fed to a phase separation vessesl (7), the mixture separating into two phases. The apparatuses usually used in industry, for example gravity separators, centrifuges or hydrocyclones, preferably decanters, may be used for phase separation. A part of the predominantly organic phase separated off is recycled via pipes (8) and (9) to the first column as column reflux. The reflux ratio is from about 0.5 to 20, preferably from about 1 to 10. The predominantly aqueous phae separated off is removed via pipe (10), and the remaining part of the organic phase is fed via pipe (11) to a second distillation column (12).

The aqueous phase separated off contains essentially water, butanol and traces of dibutyl ether. The concentrations of the individual components depend to a great extent on the actual components present. The butanol content of the aqueous phase fluctuates from about 4 to 20% by weight and the amount of dibutyl ether is not more than about 0.1% by weight. The second distillation column is operated at a higher pressure than the first distillation column. The difference between the pressures of the two columns is from about 0.05 to 5, preferably from 0.2 to 2, particularly preferably from 0.5 to 1, bar.

The temperatures in the column are from about 60 to 110° C. at the top of the column and from about 120 to 170° C. at the bottom of the column. In general, conventional columns are suitable for the separation. Conventional baffles, such as packings or trays, may be used.

The size of the column depends on the respective throughputs. The number of theoretical plates of the column is from about 5 to 50, preferably from 10 to 35, particularly preferably from 15 to 25.

In the second column, too, a product stream which advantageously has a virtually azeotropic concentration is taken off at the top via pipe (13) and condenser (14). However, owing to the pressure increase, the azeotrope now present has a lower concentration of dibutyl ether, so that a product stream which contains essentially dibutyl ether is taken off at the bottom of the column via pipe (15). Further components in this stream are butanol and traces of water.

The concentration of dibutyl ether is from about 40 to 100, preferably from 95 to 100%, by weight and may be influenced by the energy supplied to the column.

The second column is connected in a manner known per se, via pipe (16), to an evaporator (17).

The product stream taken off at the top of the second column is partly recycled to the column via pipe (18). The reflux ratio is from about 0.5 to 10, preferably from 0.6 to 3.

The remaining part of the product stream is recycled to the first column via pipe (19). This recycling may be effected both to the column feed via pipe (2) and separately to the column. Preferably, the product stream is passed into the column (1) between the feed (2) and the reflux (9). The optimum position of the feed depends on the composition of the feed stream (2) and the mode of operation of the columns (1) and (12) and may be determined by a person skilled in the art by means of routine experiments.

Particularly if the mixture freshly added to the distillation column (1) contains relatively little water, it may be advisable also to recycle to the first column parts of the aqueous phase separated off by means of the phase separation vessel. The water thus recycled may additionally act as an entraining agent for the dibutyl ether. The exact arrangement of the recycling and the amount of aqueous phase recycled depends to a great extent on the respective individual case and on the concentrations present. A reflux both at the top of the column and below the top of the column, in the rectification section or in the upper half of the stripping section may be particularly advisable.

If the fresh feed mixture contains other relatively high-boiling components in addition to butanol, water and dibutyl ether, the separation may be carried out similarly to the procedure described above. The components additionally present are virtually completely discharged in the bottom product of the first column, together with the butanol, and can then be separated off, for example by distillation. Examples of such components are 1-octanol and isodecanol. The novel process can also be used at high concentrations of these components. Advantageously, the concentrations range from about 0 to 20% by weight.

If the feed mixture contains an additional substance whose boiling point is lower than the boiling point of the ternary azeotrope, or if the feed mixture contains a substance which, together with the abovementioned substances, forms a binary, ternary or quaternary azeotrope whose boiling point is lower than the boiling point of the abovementioned ternary azeotrope, this separation problem, too, can be solved by the novel process. FIG. 2 shows an embodiment which is suitable for this case and which in many respects is similar to the embodiment shown in FIG. 1.

The embodiment illustrated in FIG. 2 is explained in more detail below. With regard to this second embodiment, reference is made to the explanations given above, unless a distinction is made below with respect to the embodiment described in FIG. 1.

A fresh feed mixture which also contains a relatively low-boiling component, referred to below as a low boiler, in addition to the components butanol, dibutyl ether and water is fed to the distillation column (1) via pipe (2). The bottom of the column is connected to an evaporator (3), and virtually pure butanol is taken off via pipe (4).

A product stream which also contains the low boiler in addition to the virtually azeotropic mixture of butanol, dibutyl ether and water is taken off at the top of the column, via pipe (5) and condenser (6).

The organic phase is removed from the phaes separation vessel (7) via pipe (8) and is partly recycled to the first column and partly fed to the second distillation column (12), via the pipes (9) and (11), respectively. The aqueous phase is removed from the phase separation vessel via pipe (10). The low boilers present in the mixture usually accumulate in particular in the organic phase. The exact concentrations depend to a great extent on the respective operating conditions and on the type of substances used and therefore cannot in general be quantified.

A side stream which also contains the low boiler in addition to the virtually azeotropic mixture is removed via pipe (13) from the second distillation column which, in the above embodiments, is operated at a higher pressure than the first column. The removal point is preferably located in the rectification section of the column, particularly preferably in the upper half of said section.

Owing to the complex influences, the amount of low boiler present in this side stream cannot in general be exactly quantified, but the concept is such that predominantly low boilers with relatively small amounts of water, butanol and dibutyl ether are removed at the top of the second column via pipe (15) and condenser (14). The amount of low boiler should be from about 30 to 99, preferably from 80 to 99%, by weight.

A predominantly aqueous phase or a phase containing predominantly low boilers is removed from the downstream phase separation vessel (16) via pipes (17) and (18).

A part of the phase containing predominantly low boilers is recycled to the column via pipe (19).

The bottom of the column is connected to an evaporator (20), and dibutyl ether of high purity is taken off via pipe (21).

The side stream removed via pipe (13) is recycled to the first column. Recycling is effected according to the first embodiment.

n-Butyraldehyde may be mentioned as an example of a low boiler. The amounts of low boiler in the feed mixture usually range from about 0.01 to 30, preferably from 0.1 to 2%, by weight.

For the embodiment described in FIG. 2, reference is otherwise made to the variant described in FIG. 1, ie. the data on pressures, geometries, concentrations, etc. given here can essentially be applied to the second variant.

Whether further phase separation vessels are used in the novel process and which positions are chosen for them depend on to what extent two phases are present and separation is desired. For example, a phase separation vessel may be advisable in stream 13 in FIG. 2.

The novel process is suitable for separating butanol and dibutyl ether from mixtures containing water, dibutyl ether and butanol. It is particularly suitable for separating off n-butanol, but 2-butanol or isobutanol and mixtures containing n-butanol and isobutanol or n-butanol and 2-butanol can also be worked up.

If mixtures which contain n-butanol and isobutanol or n-butanol and 2-butanol are to be separated, n-butanol is separated off essentially at the bottom of the first column. In this case, 2-butanol or isobutanol is to be understood as an additive which, together with dibutyl ether and water, forms an azeotrope having a lower boiling point than the mixture of n-butanol, dibutyl ether and water. In this case too, the novel process can be used according to the variant of FIG. 2. Here, the lower-boiling azeotrope is obtained as a stream (15) at the top of the column (12).

The novel process makes it possible to separate the butanol and dibutyl ether from mixtures containing butanol, water and dibutyl ether in a manner which is simple and economical in terms of process engineering. Thus, butanol with a purity greater than about 95, preferably 99.9%, by weight and dibutyl ether with a purity greater than 85, preferably 98%, by weight can be obtained. Advantageously, the introduction of additional water, which subsequently has to be separated off again by distillation, can be avoided in the novel process.

EXAMPLES

Example 1

An experiment setup according to FIG. 1 was chosen. The first column having a diameter of 50 mm has 60 bubble trays. At a reflux ratio of 3 for the organic phase and a top pressure of 250 mbar, the resulting bottom temperature is 86° C. and the resulting top temperature 71° C. The crude mixture is fed in at the 40th tray and the recycle stream at the the 50th tray. The second column is operated at a top pressure of 1 bar. At a reflux ratio of 3, the resulting bottom temperature is 146° C. and the resulting top temperature 106° C. The second column has a diameter of 43 mm. The column has 22 theoretical plates and is equipped with a structured packing. A fabric packing of the type CY from Sulzer is used. The feed is at the 8th tray. The composition of the individual streams is shown in the Table below:

|  | Stream 2 | Stream 4 | Stream 11 | Stream 10 | Stream 15 | Stream 19 |
| --- | --- | --- | --- | --- | --- | --- |
| Mass flow (kg/h) | 0.50 | 0.435 | 0.595 | 0.05 | 0.015 | 0.58 |
| n-Butanol (% by wt.) | 87.0 | 99.979 | 61.265 | 5.22 | 0.109 | 63.189 |
| Di-n-butyl ether (% by wt.) | 3.0 | 0.001 | 29.769 | 0.0 | 99.891 | 27.588 |
| Water (% by wt.) | 10.0 | 0.02 | 8.966 | 94.78 | 0.0 | 9.223 |

An experiment setup according to FIG. 2 was chosen, but no phase separation vessel was connected downstream of the second column. Feed 1 contains 1% by weight of butyraldehyde as a low boiler. The column data correspond to those in Example 1. The side stream of the second column is taken off from the 19th theoretical plate. At a top pressure of 250 mbar in the first column, the resulting bottom temperature is 87° C. and the resulting top temperature 71° C. The bottom and top temperatures of the second column at a top pressure of 1 bar are 146° C. and 80° C., respectively. The composition of the individual streams is shown in the Table below:

|  | Stream 2 | Stream 4 | Stream 11 | Stream 10 | Stream 13 | Stream 21 | Stream 18 |
| --- | --- | --- | --- | --- | --- | --- | --- |
| Mass flow (kg/h) | 0.50 | 0.43 | 0.59 | 0.05 | 0.57 | 0.015 | 0.005 |
| n-Butanol (% by wt.) | 86.0 | 99.94 | 58.49 | 5.14 | 59.97 | 0.11 | 20.30 |
| Di-n-butyl ether (% by wt.) | 3.0 | 0.006 | 30.19 | 0.0 | 28.57 | 99.87 | 25.85 |
| Water (% by wt.) | 10.0 | 0.0 | 8.30 | 94.63 | 8.76 | 0.0 | 5.68 |
| Butyraldehyde (% by wt.) | 1.0 | 0.054 | 3.02 | 0.23 | 2.70 | 0.02 | 48.17 |

Example 3

A mixture of isobutanol, di-n-butyl ether and water is distilled in a laboratory column (diameter 50 mm, packing comprising 5 mm wire mesh spirals, total height of fill 1.8 m). The mixture is fed in at a height of 1.3 m, calculated from the beginning of the packing above the bottom. The stream into the column is composed of fresh feed and of a part-stream from a distillation carried out previously. The arrangement is shown in FIG. 3. The reflux ratio of the organic phase is 5 and the top pressure is 250 mbar. The composition of the streams is shown in the Table below:

|  | Stream 1 | Stream 2 | Stream 3 | Stream 4 |
|---|---|---|---|---|
| Mass flow (kg/h) | 505 | 230 | 262 | 14 |
| Isobutanol (% by wt.) | 87 | 99.58 | 80.1 | 8 |
| Di-n-butyl ether (% by wt.) | 3 | 0.4 | 5.8 | 0 |
| Water (% by wt.) | 10 | 0.02 | 14.1 | 92 |

A mixture corresponding to the composition of stream 3 is then distilled according to FIG. 4 at 1 bar in the same column. The reflux ratio is 3. The mixture is fed in at a height of 0.5 m, calculated from the beginning of the packing above the bottom.

|  | Stream 3 | Stream 5 | Stream 6 |
|---|---|---|---|
| Mass flow (kg/h) | 262 | 249 | 14.5 |
| Isobutanol (% by wt.) | 80.1 | 85.14 | 4.87 |
| Di-n-butyl ether (% by wt.) | 5.9 | 0.63 | 95.07 |
| Water (% by wt.) | 14 | 14.23 | 0.06 |

We claim:

1. A process for separating a mixture comprising water, dibutyl ether and a butanol of the group consisting of n-butanol, 2-butanol and iso-butanol, in an apparatus comprising a first distillation column and a second distillation column, each of said distillation columns having a bottom part, a top part and a rectification section between the bottom and the top part, which process comprises
    a) introducing the mixture into the first distillation column,
    b) taking off at the bottom of the first distillation column a first fraction essentially consisting of the butanol,
    c) taking off at the top of the first distillation column a first residual mixture and optionally separating this residual mixture into an aqueous phase and an organic phase by means of a phase separation,
    d) introducing the first residual mixture or the organic phase separated from the first residual mixture into the second distillation column,
    e) taking off at the bottom of the second distillation column a second fraction essentially consisting of dibutyl ether,
    f) taking off at the top of the second distillation column a second residual mixture and optionally separating this residual mixture into an aqueous phase and an organic phase by means of a phase separation, and
    g1) recycling a part of the second residual mixture or the organic phase separated from the second residual mixture into the rectification section of the first distillation column, or
    g2) recycling a side stream which is taken off at the top part of the rectification section of the second distillation column into the rectification section of the first distillation column, which process further comprises that the second distillation column is being operated at a higher pressure than the first distillation column, and that at least one of the residual mixtures obtained in steps c) and f) is being subjected to phase separation.

2. The process of claim 1, wherein the first residual mixture is subjected to phase separation.

3. The process of claim 2, further comprising that a part of the aqueous phase is recycled into the rectification section of first distillation column.

4. The process of claim 3, wherein the side stream of the second distillation column is recycled.

5. The process of claim 2, further comprising that the side stream is separated into an aqueous phase and an organic phase.

6. The process of claim 5, further comprising that the organic phase of the side stream is recycled into the rectification section of the first distillation column.

7. The process of claim 2, wherein the side stream of the second distillation column is recycled.

8. The process of claim 3, further comprising that the side stream is separated into an aqueous phase and an organic phase.

9. The process of claim 8, further comprising that the organic phase of the side stream is recycled into the rectification section of the first distillation column.

10. The process of claim 1, wherein the side stream of the second distillation column is recycled.

11. The process of claim 1, further comprising that the side stream is separated into an aqueous phase and an organic phase.

12. The process of claim 11, further comprising that the organic phase of the side stream is recycled into the rectification section of the first distillation column.

13. The process of claim 1, wherein the first distillation column is operated at a pressure of from 0.02 to 2 bar at the top of the column.

14. The process of claim 1, wherein the second distillation column is operated at a pressure of from 0.05 to 5 bar higher than the first distillation column.

* * * * *